US012446940B2

(12) United States Patent
Aleryd et al.

(10) Patent No.: US 12,446,940 B2
(45) Date of Patent: Oct. 21, 2025

(54) TORQUE LIMITING DRIVE TOOLS

(71) Applicant: Cochlear Limited, Macquarie University (AU)

(72) Inventors: Simon Aleryd, Macquarie University (AU); Per Hillstrom, Macquarie University (AU)

(73) Assignee: Cochlear Limited, Macquarie University (AU)

( * ) Notice: Subject to any disclaimer, the term of this patent is extended or adjusted under 35 U.S.C. 154(b) by 448 days.

(21) Appl. No.: 17/916,665

(22) PCT Filed: Apr. 9, 2021

(86) PCT No.: PCT/IB2021/052638
§ 371 (c)(1),
(2) Date: Oct. 3, 2022

(87) PCT Pub. No.: WO2021/205287
PCT Pub. Date: Oct. 14, 2021

(65) Prior Publication Data

US 2023/0165615 A1 Jun. 1, 2023

Related U.S. Application Data

(60) Provisional application No. 63/007,503, filed on Apr. 9, 2020.

(51) Int. Cl.
*A61B 17/88* (2006.01)
*B25B 23/00* (2006.01)
(Continued)

(52) U.S. Cl.
CPC ...... *A61B 17/8875* (2013.01); *B25B 23/0078* (2013.01); *B25B 23/141* (2013.01);
(Continued)

(58) Field of Classification Search
CPC ... B25B 23/141; B25B 23/16; B25B 23/0078; B25B 23/1427; A61B 17/8875; A61B 2090/031; H04R 2460/17; H04R 25/606
See application file for complete search history.

(56) References Cited

U.S. PATENT DOCUMENTS 4,284,374 A * 8/1981 Senzaki .................. B23G 5/16 408/139
5,697,935 A * 12/1997 Moran .................... B25B 13/48 606/86 R
(Continued)

FOREIGN PATENT DOCUMENTS

KR 10-1225878 B1 1/2013
KR 10-1384516 B1 4/2014
(Continued)

OTHER PUBLICATIONS

International Search Report and Written Opinion in counterpart International Application No. PCT/IB2021/052638, mailed Jul. 2, 2021, 6 pages.

(Continued)

*Primary Examiner* — Zade Coley
(74) *Attorney, Agent, or Firm* — Edell, Shapiro & Finnan, LLC

(57) ABSTRACT

Presented herein are torque limiting drive tools for use with, for example, components of a medical device. A torque limiting drive tool in accordance with aspects presented herein comprises an elongate handle/body and a plurality of torque arms located at a distal end of the handle, where the plurality of torque arms define an opening configured to longitudinally (axially) receive a drive bit. The plurality of torque arms are each directly mechanically attached to the handle and are configured to exert a torque on the drive bit
(Continued)

in direct response to rotation of the elongate body in each of a first direction of rotation and a second direction of rotation.

30 Claims, 14 Drawing Sheets

(51) Int. Cl.

| | |
|---|---|
| ***B25B 23/14*** | (2006.01) |
| ***B25B 23/142*** | (2006.01) |
| ***B25B 23/16*** | (2006.01) |
| *A61B 90/00* | (2016.01) |

(52) U.S. Cl.

CPC .......... *B25B 23/1427* (2013.01); *B25B 23/16* (2013.01); *A61B 2090/031* (2016.02)

(56) References Cited

U.S. PATENT DOCUMENTS

| | | | | |
|---|---|---|---|---|
| 6,439,086 | B1 * | 8/2002 | Bahr | B25B 23/1427 81/473 |
| 7,243,580 | B2 * | 7/2007 | Frazee | A61B 17/8875 81/439 |
| 7,630,750 | B2 | 12/2009 | Liang et al. | |
| 7,762,164 | B2 * | 7/2010 | Nino | B25B 23/1427 81/475 |
| 8,617,174 | B2 | 12/2013 | Axelson, Jr. et al. | |
| 10,194,988 | B2 * | 2/2019 | Schaller | F16D 7/002 |
| 10,219,853 | B2 * | 3/2019 | Nino | B25B 23/142 |
| 2003/0208099 | A1 | 11/2003 | Ball | |
| 2004/0015070 | A1 | 1/2004 | Liang et al. | |
| 2004/0127888 | A1 * | 7/2004 | O'Neil | A61B 90/36 606/1 |
| 2005/0148905 | A1 * | 7/2005 | Frazee | A61B 17/8875 601/2 |
| 2009/0043556 | A1 | 2/2009 | Axelson et al. | |
| 2010/0211115 | A1 * | 8/2010 | Tyber | A61B 17/863 606/305 |
| 2010/0251861 | A1 * | 10/2010 | Sixto, Jr. | B25B 23/1427 81/436 |
| 2012/0071890 | A1 | 3/2012 | Taylor et al. | |
| 2013/0165737 | A1 | 6/2013 | Van den Heuvel | |
| 2014/0276002 | A1 | 9/2014 | West et al. | |
| 2014/0276893 | A1 * | 9/2014 | Schaller | B25G 3/02 606/104 |
| 2014/0324458 | A1 | 10/2014 | Carpenter et al. | |
| 2014/0366691 | A1 * | 12/2014 | Ivinson | A61B 90/03 81/475 |
| 2015/0088225 | A1 | 3/2015 | Noble et al. | |
| 2015/0202018 | A1 * | 7/2015 | Schaller | F16D 7/002 81/467 |

FOREIGN PATENT DOCUMENTS

| | | | |
|---|---|---|---|
| WO | 99-02870 | A1 | 1/1999 |
| WO | 2019-082889 | A1 | 5/2019 |
| WO | 2001056491 | A2 | 8/2021 |

OTHER PUBLICATIONS

Campbell, Luke et al., "Intraoperative Real-time Cochlear Response Telemetry Predicts Hearing Preservation in Cochlear Implantation", Otology & Neurotology, vol. 37, No. 4, 2016, 7 pages.

Med-El, "Otoplan: The Future of Otological Surgery", Feb. 21, 2018, https://blog.medel.pro/otoplan-future-otological-surgery/, 13 pages.

Liu, Houguang et al., "The Influence of Piezoelectric Transducer Stimulating Sites on the Performance of Implantable Middle Ear Hearing Devices: A Numerical Analysis", Micromachines 2019, 10, 782; doi:10.3390/mi10110782, 16 pages.

Ircad France, "Visible Patient", https://www.ircad.fr/research/visible-patient/, downloaded Mar. 20, 2020, 4 pages.

* cited by examiner

TORQUE LIMITING DRIVE TOOLS

BACKGROUND

Field of the Invention

The present invention relates generally to a torque limiting drive tools for use with medical devices.

Related Art

Medical devices have provided a wide range of therapeutic benefits to recipients over recent decades. Medical devices can include internal or implantable components/devices, external or wearable components/devices, or combinations thereof (e.g., a device having an external component communicating with an implantable component). Medical devices, such as traditional hearing aids, partially or fully-implantable hearing prostheses (e.g., bone conduction devices, mechanical stimulators, cochlear implants, etc.), pacemakers, defibrillators, functional electrical stimulation devices, and other medical devices, have been successful in performing lifesaving and/or lifestyle enhancement functions and/or recipient monitoring for a number of years.

The types of medical devices and the ranges of functions performed thereby have increased over the years. For example, many medical devices, sometimes referred to as "implantable medical devices," now often include one or more instruments, apparatus, sensors, processors, controllers or other functional mechanical or electrical components that are permanently or temporarily implanted in a recipient. These functional devices are typically used to diagnose, prevent, monitor, treat, or manage a disease/injury or symptom thereof, or to investigate, replace or modify the anatomy or a physiological process. Many of these functional devices utilize power and/or data received from external devices that are part of, or operate in conjunction with, implantable components.

SUMMARY

In one aspect, a torque limiting drive tool is provided. The torque limiting drive tool comprises: an elongate handle having a proximal end and a distal end; and at least first and second torque arms located at the distal end of the elongate handle and defining a bore configured to longitudinally receive a drive bit therein, wherein the at least first and second torque arms are each directly mechanically attached to the handle and configured exert a torque on the drive bit in direct response to rotation of the elongate handle in each of a first direction of rotation and a second direction of rotation, and wherein the torque exerted by the at least first and second torque arms has an associated first maximum torque limit in the first direction of rotation and an associated second maximum torque limit in the second direction of rotation.

In another aspect, a torque limiting drive tool is provided. The torque limiting drive tool comprises: a body having an elongate axis of rotation; an opening at a first end of the body configured to receive a drive bit along the axis of rotation; and a plurality of torque arms substantially surrounding the opening, wherein the plurality of torque arms are configured to grip the drive bit within the opening and to exert up to a first maximum rotational force on the drive bit in a first rotational direction and up to a second maximum rotational force on the drive bit in a second rotational direction.

In another aspect, a medical tool is provided. The medical tool comprises: a handle having an axis of rotation; and two or more torque arms located at a distal end of the handle and forming a bore to receive a drive bit along the axis of rotation, wherein the two or more torque arms are each connected to the handle and biased towards the bore to exert an torque on the drive bit in direct response to rotation of the handle about the axis of rotation, and wherein the torque exerted by the two or more torque arms has an asymmetrical torque limit about the axis of rotation.

In another aspect, a torque limiting drive tool is provided. The torque limiting drive tool comprises: an elongate handle having a first end, a second end, an outer surface, and an inner surface; and a plurality of torque arms disposed at the distal end of the elongate handle, wherein the plurality of torque arms have a first end and a second end, wherein the first ends of each of the plurality of torque arms attached to the inner surface of the housing and each extend a transverse distance from the inner surface to the second ends of the plurality of torque arms, wherein the plurality of torque arms each have a curved cross-sectional shape within a plane that is generally transverse to an elongate axis of the handle, wherein the second ends of the plurality of torque arms define a bore configured to longitudinally receive a drive bit therein, wherein the plurality of torque arms have symmetrical shapes, but are oriented in opposing directions such the second ends of each of the plurality of torque arms are configured exert a torque on the drive bit in direct response to rotation of the elongate handle in each of a first direction of rotation and a second direction of rotation, and wherein the torque exerted by the plurality of torque arms has an associated first maximum torque limit in the first direction of rotation and an associated second maximum torque limit in the second direction of rotation.

BRIEF DESCRIPTION OF THE DRAWINGS

Embodiments of the present invention are described herein in conjunction with the accompanying drawings, in which.

DETAILED DESCRIPTION

Presented herein are torque limiting drive tools for use with, for example, components of a medical device. A torque limiting drive tool in accordance with aspects presented herein comprises an elongate handle/body and a plurality of torque arms located at a distal end of the handle, where the plurality of torque arms define an opening or bore configured to longitudinally (axially) receive a drive bit. The plurality of torque arms are each directly mechanically attached to the handle and are configured to exert a torque on the drive bit in direct response to rotation of the elongate body in each of a first direction of rotation and a second direction of rotation. The torque exerted by the plurality of torque arms has an associated first maximum torque limit in the first direction of rotation and an associated second maximum torque limit in the second direction of rotation. In certain embodiments, the second maximum torque limit is greater than the first maximum torque limit.

Merely for ease of description, the torque limiting drive tools presented herein are primarily described herein with reference to a percutaneous bone conduction device. However, it is to be appreciated that the torque limiting drive tools presented herein may also be used with a variety of other devices/systems, including other implantable medical devices/systems. For example, the torque limiting drive tools presented herein may be used with other auditory prostheses, including other bone conduction devices, cochlear implants, middle ear auditory prostheses, direct acoustic stimulators, auditory brain stimulators, etc. The torque limiting drive tools presented herein may also be used with bone screws, vestibular devices (e.g., vestibular implants), visual devices (i.e., bionic eyes), sensors, pacemakers, drug delivery systems, defibrillators, functional electrical stimulation devices, catheters, seizure devices (e.g., devices for monitoring and/or treating epileptic events), sleep apnea devices, electroporation devices, etc.

Figure 1A:
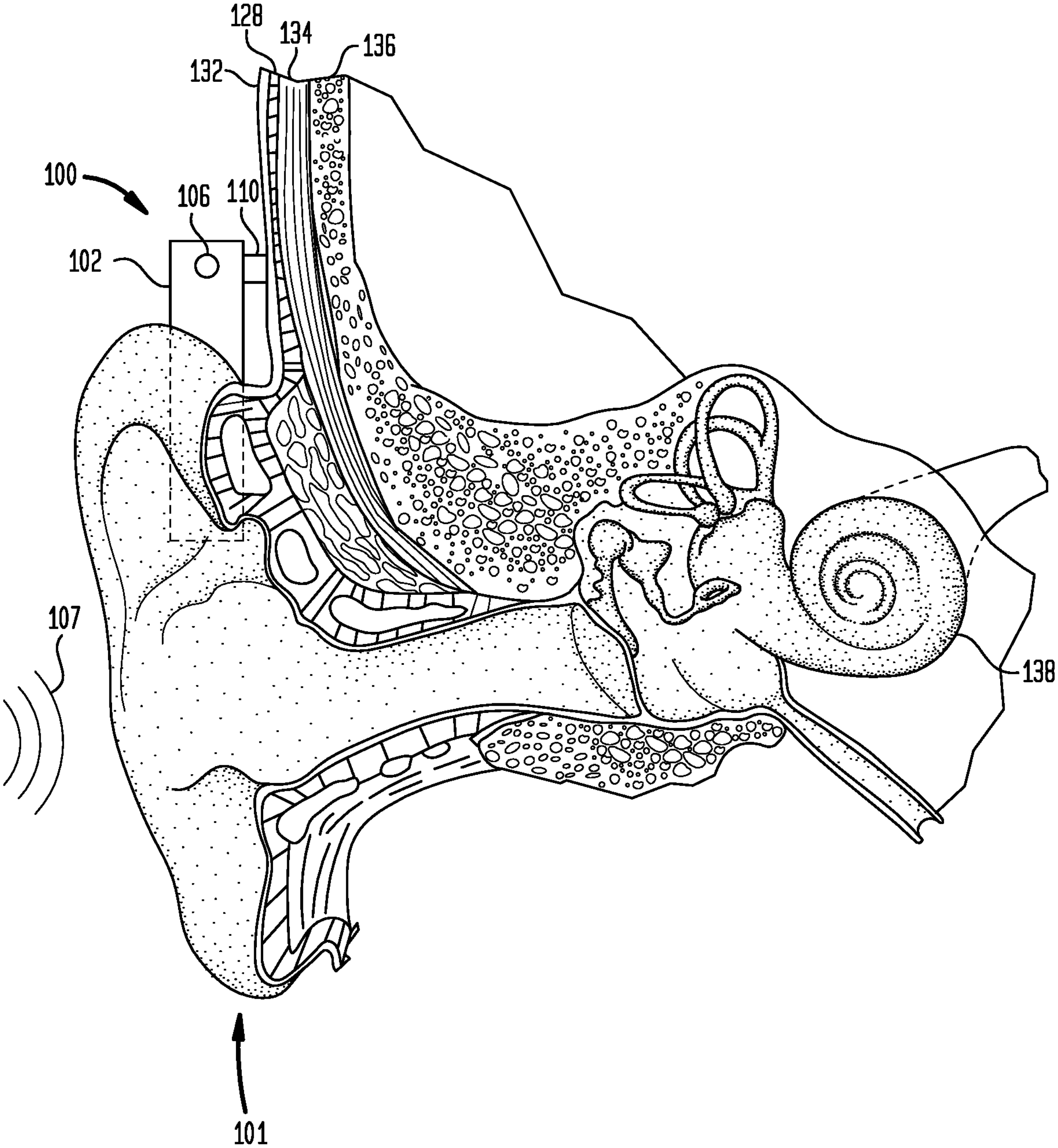
FIG. 1A is a perspective view of a percutaneous bone conduction device for use with a torque limiting drive tool, in accordance with certain embodiments presented herein.

FIG. 1A is a perspective view of a percutaneous bone conduction device 100 that can be used with a torque limiting drive tool presented herein. In the example of FIG. 1A, the percutaneous bone conduction device 100 is shown positioned behind outer ear 101 of the recipient. The bone conduction device 100 comprises a housing 102 and one or more sound input elements 106 that are configured to receive sound signals 107. The sound input element(s) 106 can comprise, for example, microphones, telecoils, ports, a wireless interface, etc. Shown in FIG. 1A is a sound input element 106 in the form of a microphone positioned on the housing 102. However, it is to be appreciated that, in other examples, one or more sound input elements may also or alternatively be located in the housing 102, on a cable extending from the housing 102, etc. The housing 102 of bone conduction device 100 also comprises a sound processor (not shown), a vibrating actuator, and/or the operational components, as needed (e.g., battery, wireless communication circuitry, etc.).

In operation, at least one of the one or more sound input elements 106 receives sound signals, such as sound signals 107. If not already in electrical form, the at least one sound input element 106 converts the received sound signals into electrical signals. The sound processor then converts the electrical signals into actuator control signals that cause the actuator to vibrate. That is, the actuator converts the electrical actuator control signals into mechanical force that imparts vibrations to the skull bone 136 of the recipient. When imparted to the skull bone 136, the vibrations causes motion of the fluid within cochlea 138 of the recipient, which in turn induces a hearing sensation (i.e., enables the recipient to receive the sound signals received at the at least one sound input element 106).

As shown, the bone conduction device 100 further includes a coupling apparatus 110 that attaches the bone conduction device 100 to the recipient. In the example of FIG. 1A, the coupling apparatus 110 is attached to an anchor system (not shown) implanted in the recipient. An exemplary anchor system (also referred to as a fixation system) may, for example, include a percutaneous abutment fixed to the recipient's skull bone 136. The abutment extends from skull bone 136 through muscle 134, fat 128 and skin 132 so that coupling apparatus 110 may be attached thereto. Such a percutaneous abutment provides an attachment location for coupling apparatus 110 that facilitates efficient transmission of mechanical force to the skull bone 136.

Figure 1B:
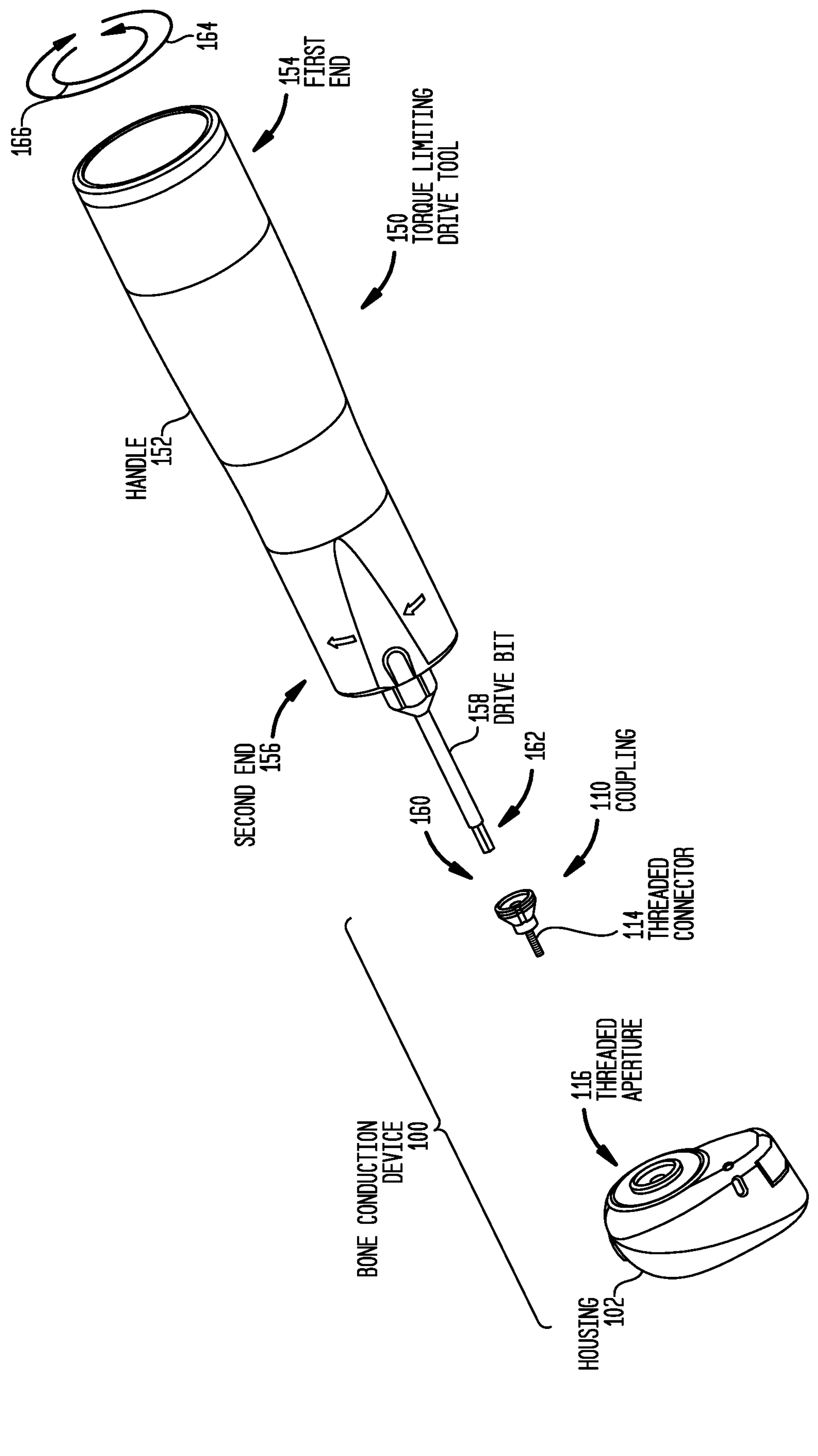
FIG. 1B is a perspective view of the percutaneous bone conduction device of FIG. 1A and a torque limiting drive tool, in accordance with certain embodiments presented herein.

FIG. 1B is perspective view of the bone conduction device 100 shown separated from the head of the recipient. In addition, in FIG. 1B, the housing 102 of the bone conduction device 100 is shown separated from the coupling 110. As described further below, FIG. 1B also illustrates a torque limiting drive tool 150, in accordance with aspects presented herein.

As shown, the coupling apparatus 110 comprises a threaded connector (bolt) 114 having male screw threads. The housing 102 includes a threaded bore 116 having female screw threads that are configured to mate with the male screw threads of the threaded connector 114. That is, the threaded connector 114 is configured to be fastened (threaded) into the threaded bore 116 to form a threaded joint (threaded connection).

As noted, the coupling apparatus 110 includes the threaded connector 114 that is configured to be threaded into the threaded bore 116. In other words, the threaded connector 114 includes male screw threads that are configured to mate with female screw threads of the threaded bore 116. When the threaded connector 114 is inserted into the threaded bore 116, the threaded connector 114 and the threaded bore 116 collectively form a "threaded-fastener joint," "screw joint" or simply "threaded joint."

A critical factor when it comes to reliability of a threaded-joint is "preload," which refers to the force that the tightened fastener exerts on an assembly. Preload is a function of many variables, but is affected by the tightening torque applied when forming the threaded-joint. The tension on a fastener for a given preload and external load is given as shown below in Equation 1:

$$P_t=P_i=P_e(K_s/(K_s+K_c)) \quad \text{Equation 1}$$

Where, $K_c$=Assembly spring constant, lb./in;

$K_s$=Screw spring constant, lb/in.

$P_e$=External payload, lb.

$P_i$=Preload, lb.

$P_t$=Total bolt load, lb.

In addition, when fasteners are torqued to increase preload, torsional stresses placed on the fasteners reduce the tensile force they can exert before yielding. The total tensile stress felt by the threaded connector (bolt) is given as shown below in Equation 2.

$$S_t=P_t/2A+((P_t/2A)^2-(tr/J)^2)^{0.5} \quad \text{Equation 2}$$

Where,

A=Thread stress area (in.$^2$),

Polar moment of inertia, pi*r4/2, $K_c$=Assembly spring constant, lb./in., $P_t$=Total bolt load, lb., $S_t$=Total tensile stress felt by bolt, psi, and t=Torsion felt by screw, lb.-in.

The required tightening torque for the fastener can be estimated from the empirical expression for the fastener, given below in Equation 3.

$$T=KDP_t \quad \text{Equation 3}$$

Where,

K=Constant from 0.05 to 0.35,

D=Nominal screw diameter (in.), and $P_t$=Total bolt load, lb.

As illustrated above, controlling the torque which a fastener is tightened is an important factor in controlling preload. Applying a correct/proper amount of torque, and accordingly achieving a correct preload for a threaded joint, is important for medical devices, such as bone conduction device 100. For example, insufficient preload caused by application of insufficient (e.g., too little) tightening torque, referred to as "undertorquing," could cause the threaded connector 114 to separate from the threaded bore 116. Undertorquing could allow the threaded connector 114 to work itself free from, and disengage, the threaded bore 116. Undertorquing the threaded connector 114 may also allow the threaded joint to flex and thus fail under fatigue.

Similarly, applying too much tightening torque, referred to as "overtorquing," can subject a threaded joint to "overloading." Overloading, through overtorquing of threaded connector 114 into the threaded bore 116, could produce loads that exceed the clamp load, causing the threaded joint to loosen over time or fail catastrophically (e.g., result in torsional stresses placed on the fasteners reduce the tensile force they can exert before yielding). In other words, overloading increases the torsional stresses placed on the fasteners, thereby reducing the tensile force they can exert before yielding. In addition, overtorquing may cause failure by damaging or deforming the male threads of threaded connector 114 and/or the female screw threads of threaded bore 116.

Overtorquing the threaded connector 114 could also damage the housing 102 or other components of bone conduction device 100. For example, applying too much force to the threaded connector 114 could cause the housing 102 to crack or otherwise fail, or result in damage to components within the housing 102.

If the threaded joint formed by threaded connector 114 and threaded bore 116 were to fail or disengage (e.g., as a result of undertorquing or overtorquing) while the bone conduction device 100 is worn by the recipient, not only could the bone conduction device 100 be damaged (e.g., through impact with the ground or other surface), but the recipient would also lose the ability to hear (at least until the bone conduction device 100 can be re-attached and/or repaired, if necessary).

Tools have been developed to ensure a threaded connector is subject to the correct amount of torque during formation of a threaded joint. However, such tools are often complex, expensive, and/or not suitable for use with medical devices. Accordingly, presented herein are simple torque limiting drive tools, such as tool 150 of FIG. 1B, that are suitable for use with medical devices. As described below, torque limiting drive tools in accordance certain embodiments presented herein may be re-usable or configured as a single-use, sterilized tool. The torque limiting drive tools in accordance certain embodiments presented herein may be produced as a unitary (one-piece) polymeric structure at a low cost (e.g., injection molding, milling, etc.). In addition, the torque limit may be fixed into the design.

In the example of FIG. 1B, the torque limiting drive tool 150 includes an elongate handle (body) 152 having a first (proximal) end 154 and a second (distal) end 156. The second end 156 includes a bore (not shown in FIG. 1B) that is defined/formed by at least two torque arms (also not shown in FIG. 1B). The bore is configured to receive a drive bit 158 that is useable to attach the coupling 110 to the housing 102 (i.e., thread threaded connector 114 into the threaded bore 116). In particular, the coupling 110 has a screw head 160 (e.g., torx head, hex head, Phillips head, Robertson head, etc.) that is configured to receive and mate with a distal drive head 162 of the drive bit 158.

As described further below, when the distal drive head 162 is mated with the screw head 160, rotation of the handle 152 in a first (e.g., clockwise) direction of rotation, generally shown by arrow 164, exerts a torque on the threaded connector 114 that causes the threaded connector 114 to advance into the threaded bore 116. Similarly, when the distal drive head 162 is mated with the screw head 160, rotation of the handle 152 in a second (e.g., counter-clockwise) direction of rotation, generally shown by arrow 166, exerts a torque on the threaded connector 114 that causes the threaded connector 114 to retract from the threaded bore 116. Also as described below, a torque limiting drive tool presented herein, such as torque limiting drive tool 150, is configured such that the tool can only exert a limited amount of torque on the threaded connector 114 in each of the first direction 164 and the second direction 166. In certain embodiments, the torque limiting drive tool 150 is configured such that the amount of torque exerted on the threaded connector 114 in each of the first direction 164 and the second direction 166 is substantially the same. However, in other embodiments, the torque limiting drive tool 150 is configured such that the amount of torque applied the second direction 166 is greater than the amount of torque exerted in the first direction 164.

As noted, FIGS. 1A and 1B generally illustrate use of the torque limiting drive tool 150 used with bone conduction device 100, namely for securing the coupling 110 to the housing 102. It is to be appreciated that such use of the torque limiting drive tool 150, and more generally of torque limiting drive tools in accordance with embodiments presented herein, is merely illustrative. In particular, it is to be appreciated that torque limiting drive tools in accordance with certain embodiments presented herein could be used in a number of different manners for a number of different purposes. For example, torque limiting drive tools in accordance with certain embodiments presented may be particularly beneficial in the implanting context as they can give rise to a single-use, sterile tool that can act to reduce instances of infection, etc. In one such illustrative example, torque limiting drive tools in accordance with embodiments presented herein could be used to implant fixation systems, such as bone screws, in the body of the recipient.

For example, as noted above, the coupling 110 is configured for attachment to a fixation system, which include a percutaneous abutment fixed to the recipient's skull bone 136. The abutment may be fixed to the recipient's skull bone 136 via a bone screw. In certain examples, a torque limiting drive tool in accordance with certain embodiments presented herein may be configured for use in implanting (e.g., screwing) such a bone screw into the skull bone 136.

Figure 2A:
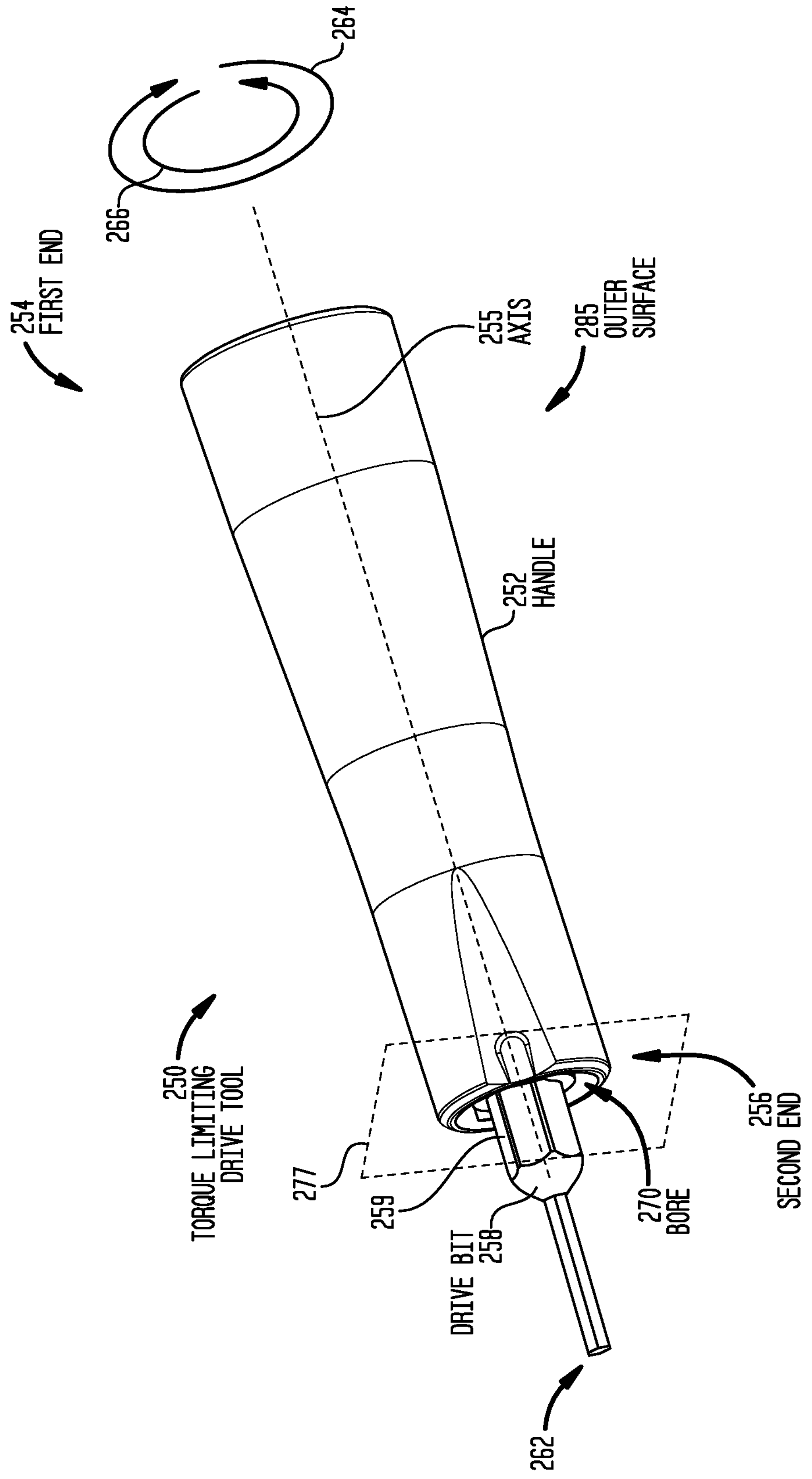
FIG. 2A is a perspective view of a torque limiting drive tool, in accordance with certain embodiments presented herein.
Figure 2B:
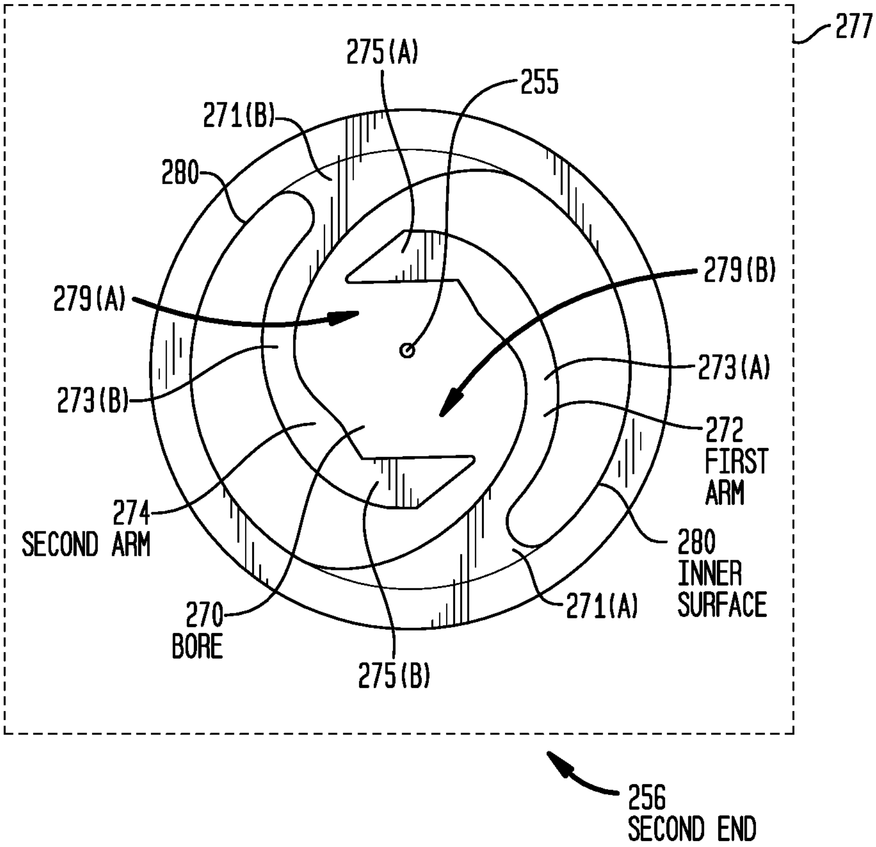
FIG. 2B is top-view of a distal end of the torque limiting drive tool of FIG. 2A, in accordance with certain embodiments presented herein.
Figure 2C:
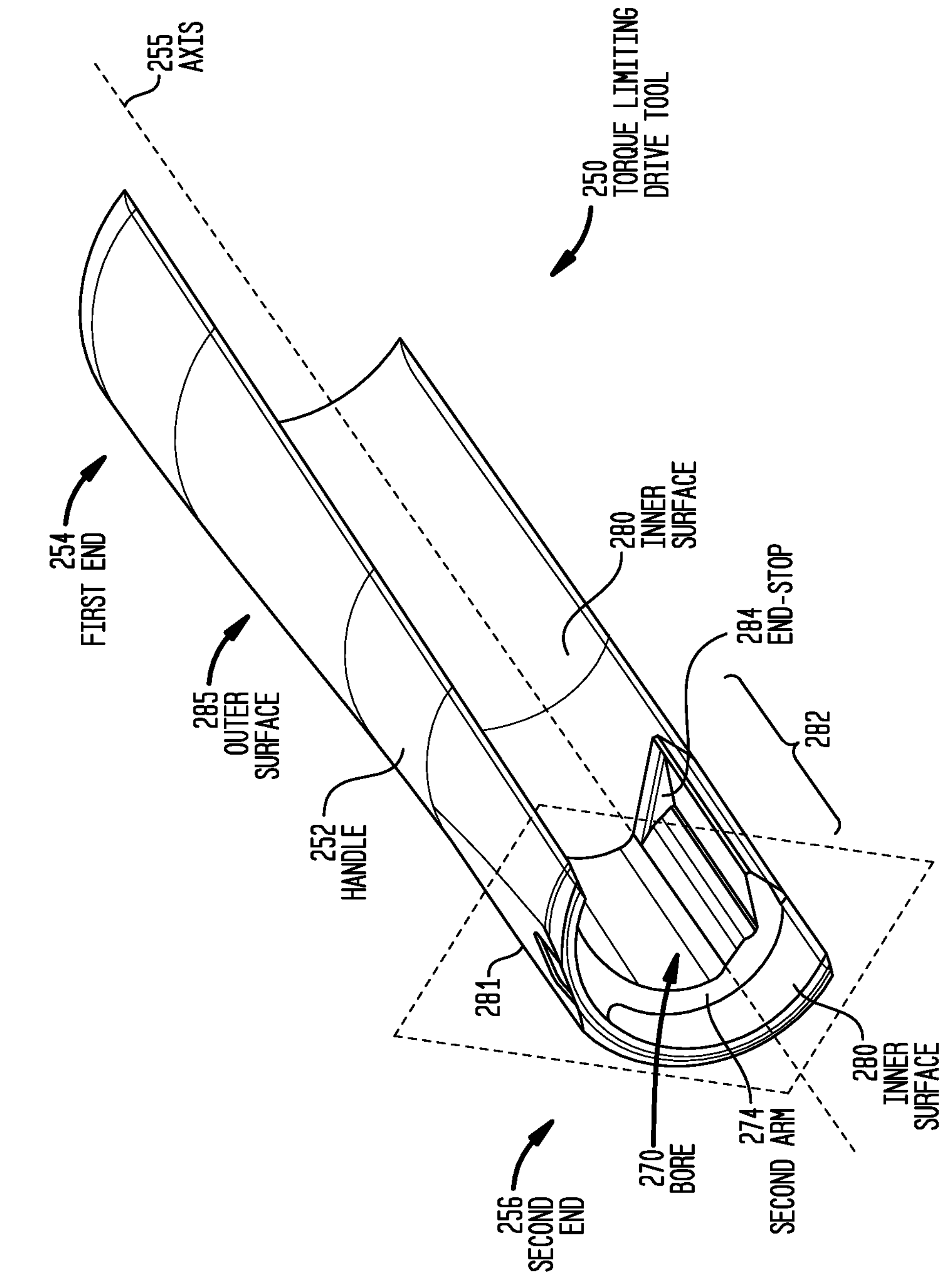
FIG. 2C is a first cross-sectional view of the torque limiting drive tool of FIG. 2A, in accordance with certain embodiments presented herein.
Figure 2D:
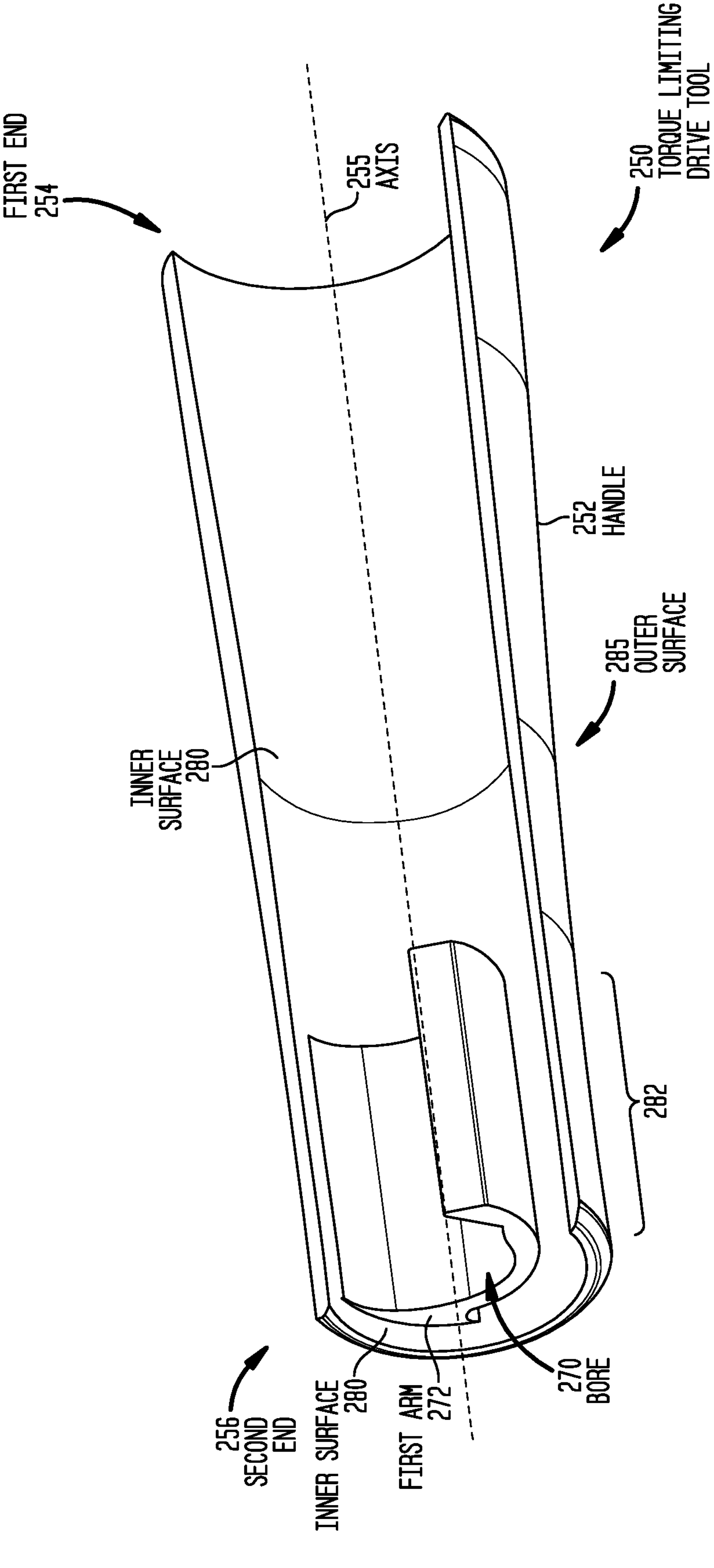
FIG. 2D is a second cross-sectional view of the torque limiting drive tool of FIG. 2A, in accordance with certain embodiments presented herein.
Figure 2E:
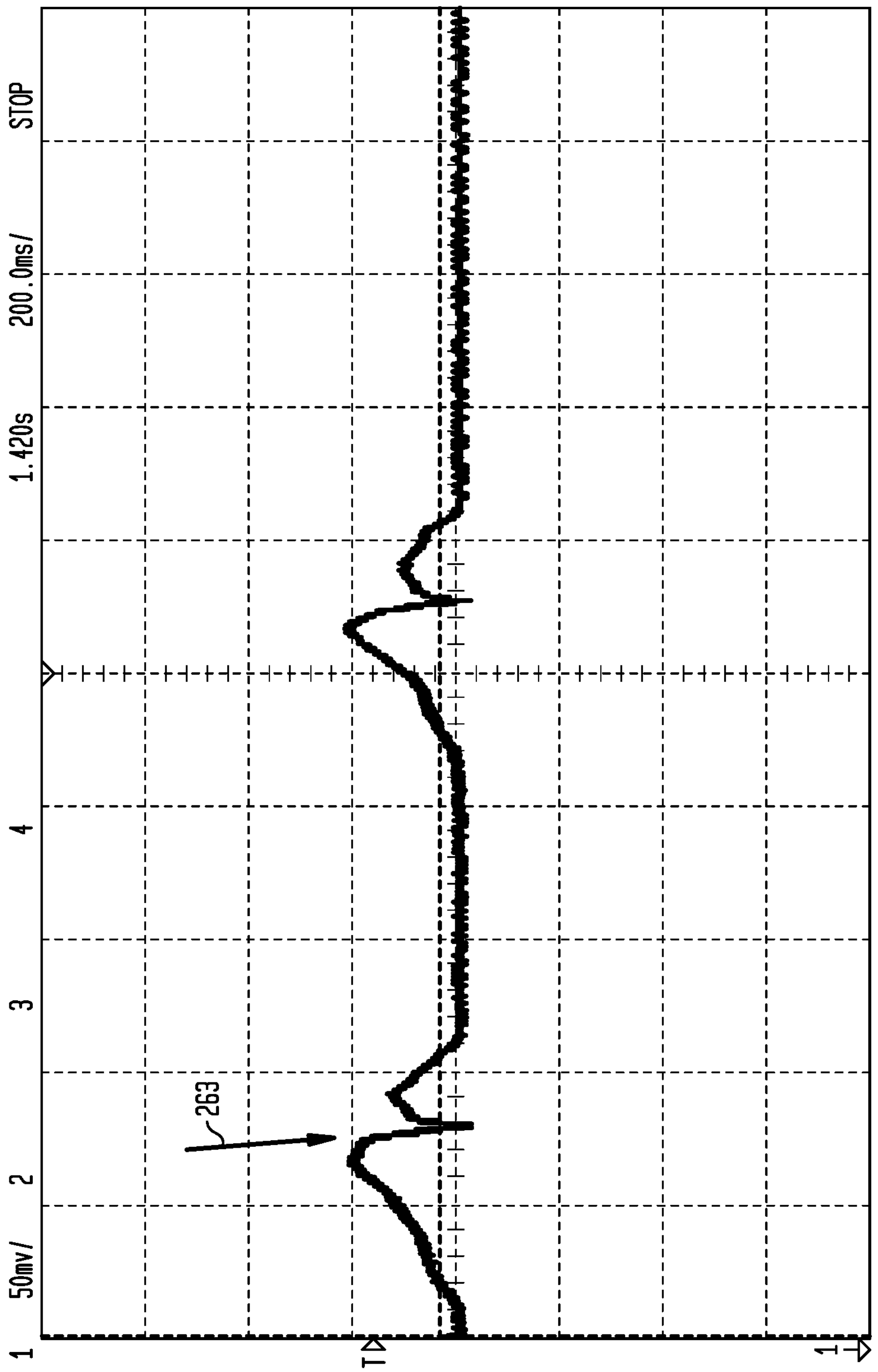
FIG. 2E is a graph illustrating rotation of a torque limiting drive tool around a drive bit, in accordance with embodiments presented herein.

FIGS. 2A-2E are schematic diagrams illustrating further details of a torque limiting drive tool, referred to as torque limiting drive tool 250, in accordance with certain embodiments presented herein. FIG. 2A is a perspective view of the torque limiting drive tool 250 shown with a drive bit 258, while FIG. 2B is a top view of a distal end of the torque limiting drive tool 250 from which the drive bit 258 has been removed. FIGS. 2C and 2D are different cross-sectional views of the as torque limiting drive tool 250. FIG. 2E is a graph illustrating rotation of the torque limiting drive tool 250 around the drive bit 258. For ease of reference, FIGS. 2A-2E will be generally described together.

As shown, the torque limiting drive tool 250 comprises an elongate handle (body) 252 having a first (proximal) end 254 and a second (distal) end 256. The second end 256 includes a bore (aperture or opening) 270 that is defined/formed by a plurality of torque arms. In the examples of FIGS. 2A-2E, the plurality of torque arms comprise a first torque arm 272 and a second torque arm 274. However, as described further below, certain embodiments presented herein may include more than two torque arms.

The bore 270 is configured (e.g., shaped and dimensions) so as to longitudinally (axially) receive a drive bit 258 therein. That is, the handle 252 has an elongate central axis 255 and the bore 270 is positioned such that the drive bit 258 may be received along, or generally parallel to, the elongate axis 255 (e.g., the bore 270 centered on the elongate central axis 255 or offset from the elongate central axis 255).

As noted, the bore 270 is defined/formed by the first torque arm 272 and the second torque arm 274. As shown in FIG. 2B, the first torque arm 272 has a first (primary) end 271(A) and a second (secondary) end 275(A) that are connected by a central region 273(A). The first torque arm 272 has a general arched or curved cross-sectional shape (e.g., along/within/parallel to a plane 277 that is generally transverse to elongate axis 255) extending from the first end 271(A) to the second end 275(A). However, as shown, the second end 275(A) has a cross-sectional thickness that is greater than a cross-sectional thickness of the central region 273(A). Similarly, the first end 271(A) has a tapered cross-sectional shape from an inner surface 280 of the handle 252 to the central region 273(A). In other words, torque arm 272 has varying thickness along the transverse/lateral direction of the arm (i.e., in the direction along/within/parallel to the plane 277). In addition, the second end 275(A) includes a planar surface 279(A) facing (and at least partially defining) the bore 270.

Similarly, the second torque arm 274 has a first (primary) end 271(B) and a second (secondary) and 275(B) that are connected by a central region 273(B). The second torque arm 274 also has a general arched or curved cross-sectional shape (e.g., along/within/parallel to the plane 277 that is generally transverse to elongate axis 255) extending from the first end 271(B) to the second end 275(B). However, as shown, the second end 275(B) has a cross-sectional thickness that is greater than a cross-sectional thickness of the central region 273(B). Similarly, the first end 271(B) has a tapered cross-sectional shape from the inner surface 280 of the handle 252 to the central region 273(B). In other words, torque arm 274 has varying thickness along the transverse/lateral direction of the arm (i.e., in the direction along/within/parallel to the plane 277). In addition, the second end 275(B) includes a planar surface 279(B) facing (and at least partially defining) the bore 270.

In the embodiment of FIGS. 2A-2D, the torque arms 272 and 274 have generally symmetrical shapes, but are rotated relative to another. As a result, the planar surfaces 279(A) and 279(B) face one another across the bore 270. In addition, the first ends 271(A) and 271(B) of torque arms 272 and 274, respectively, are each attached to, and extend from, an inner surface 280 of the handle 252. That is, the first and second torque arms 272, 274 are each directly mechanically attached to the inner surface 280 of the handle 252.

As shown, the first torque arm 272 and the second torque arm 274 each extend a transverse distance from the inner surface 280 of the handle 252. That is, the first torque arm 272 and the second torque arm 274 each extend from the inner surface 280 of the handle 252 in a direction that is generally orthogonal to the elongate axis 255 (e.g., along/within/parallel to the plane 277). As such, the torque limiting drive tool 250 is referred to as having a closed outer design that allows a user to grip the tool anywhere without influencing the torque limit. That is, in this arrangement, the torque arms 272 and 274 are isolated from the outer surface where the user holds the device and, accordingly, the torque arms are isolated from the grip of the user (i.e., non-sensitive to where the device is held).

As noted, bore 270 is configured to axially/longitudinally receive the drive bit 258 therein. The bore 270 has a size (e.g., dimensions) and shape, formed by the torque arms 272 and 274, that generally corresponds to the size and shape of outer surface 259 of the drive bit 258 (e.g., the bore 270 is configured to mate with the drive bit 258. In addition, the torque arms 272 and 274 are each biased towards the center (e.g., axis 255) of the bore 270 so as to grip the drive bit 258 when the drive bit 258 is inserted into the bore.

As shown in FIGS. 2C and 2D, the torque arms 272 and 274 each have a length 282 extending longitudinally/axially into the handle 252 (e.g., a length that is generally parallel to the elongate axis 255). One or both of the torque arms 272 and 274 also includes an end-stop 284 that terminates the insertion of the drive bit 258 into the housing 252. That is, the drive bit 258 is inserted into bore 270, the end of the drive bit 258 will be positioned abutting the end-stop(s) 284. In this position, the entire length 282 of each of the torque arms 272 and 274 will be abutting the outer surface 259 of the drive bit 258. As such, when the drive bit 258 is fully inserted into the bore 270 (inserted such that the end of the drive bit 258 abuts the end-stop(s) 284), the bias of the torque arms 272 and 274 (along the entire length 282 thereof) cause the torque arms to apply a compressive force on the outer surface 259 of the drive bit 258 (e g., to grip the drive bit).

Once the drive bit 258 is fully inserted into the bore 270, a distal drive head 262 of the drive bit is mated with a screw head of a component of a medical device. In operation, a user applies a manual rotation force to an outer surface 285 of the handle 252 to cause the handle to rotate in either a first direction of rotation, represented by arrow 264 in FIG. 2A, or a second direction of rotation, represented by arrow 266 in FIG. 2B. Since the torque arms 272 and 274 are directly mechanically attached to the inner surface 280, and because the torque arms 272 and 274 are abutting the drive bit 258, rotation of the handle 252 in either the first direction of rotation 264 or the second direction of rotation 266 will cause corresponding rotation of the drive bit 258 in the same rotational direction. That is, the torque arms 272 and 274 are configured (e.g., biased towards the opening) so as to exert a torque on the drive bit 258 in direct response to rotation of the handle 252 in each of the first direction of rotation 264 or the second direction of rotation 266. However, the torque arms 272 and 274 are also configured such that only a limited amount of torque may be applied to the drive bit 258 in each of the first direction of rotation 264 and the second direction of rotation 266.

More specifically, the torque arms 272 and 274 are configured such that if the torque (rotational force) exerted by the handle 252 onto the drive bit 258 (via the torque arms 272 and 274) exceeds a predetermined threshold, sometimes referred to as a "maximum rotational force" or a "maximum torque limit," then the torque arms 272 and 274 (e.g., the entire elongate length 282 of the arms) will deflect/flex away from the bore 270 (and the outer surface 259 of the drive bit 258). This deflection of the torque arms 272 and 274 causes the torque arms (and attached handle 252) to slip or rotate around the outer surface 259 of the drive bit 258 (e.g., "step-over" a portion of the outer surface 259). Therefore, since the torque arms 272 and 274 rotate around the outer surface 259 (and at the same time the drive bit 258 does not rotate), the torque arms are unable to apply any additional torque to the drive bit 258.

The rotation of the torque arms 272 and 274, and the attached handle, around the outer surface 259 of the drive bit 258, without corresponding rotation of the drive bit 258 itself, provides the user with a haptic indication that the maximum torque limit has been reached (e.g., the user can manually feel the relatively free spinning of the handle 252). However, the rotation of the torque arms 272 and 274 around the outer surface 259 of the drive bit 258 may also emit an audible "click" sound, which provides the user within an audible indication that the maximum torque limit has been reached. That is, the tool 250 is configured such that reaching the maximum torque limit causes a sudden drop in the torque when the torque arms "steps over" (e.g., rotate around) the drive bit 258. This provides not only a clear audible sound, but also detectable haptic feedback. In the graph of FIG. 2E, arrow 263 illustrates a negative derivative occurring when the torque arms 272 and 274 rotate around (step-over) the drive bit 258, which accordingly provides the haptic and audible indications that the maximum torque limit has been reached.

In the embodiments of FIGS. 2A-2D, the material properties, structural arrangement, and relative orientation of the torque arms 272 and 274 determine/set the maximum torque limit in each of the direction of rotation 264 or the second direction of rotation 266. In certain embodiments, the torque arms 272 and 274 are configured such that the maximum amount of torque that may be exerted on the drive bit 258 in each of the first direction of rotation 264 and the second direction of rotation 266 is substantially the same. However, in other embodiments, such as that shown in FIGS. 2A-2D, the torque arms 272 and 274 are configured such that the maximum amount of torque that may be exerted in the second direction of rotation 266 is greater than the amount of torque exerted in the first direction of rotation 264. The ability to provide a different amount of torque in each of the first direction of rotation 264 and the second direction of rotation 266 is sometimes referred to herein as an "asymmetrical torque limit."

In the example of FIGS. 2A-2D, the asymmetrical torque limit is a result of the relative orientation of the torque arms 272 and 274. In particular, as shown in FIG. 2B, the torque arms 272 and 274 are substantially identical, but the torque arms 272 and 274 are oriented (pointed) in different directions. This difference in orientation causes the torque arms 272 and 274 to operate differently with rotation in each of the first direction of rotation 264 and the second direction of rotation 266.

More specifically, as the handle 252 is rotated in the first direction of rotation 264, the torque arms 272 and 274 have a predisposition/tendency to flex outward from the center of the bore 255 (e.g., flex away from axis 255 as a result of the rotation in the first direction of rotation). However, as the handle 252 is rotated in the second direction of rotation 266, the torque arms 272 and 274 have a predisposition/tendency to flex inward towards the center of the bore 255 (e.g., flex towards axis 255 as a result of the rotation in the second direction of rotation). These different predispositions (i.e., to flex outward in the first direction of rotation and to flex inward in the second direction of rotation) results in different maximum torque limits in each of the two directions. The predisposition to flex inward in the second direction of rotation 266 increases the torque that can be applied by the torque arms 272 and 274 before the torque arms begin to slip/rotate around the outer surface 259 of the drive bit 258. In certain examples, with two substantially identical torque arms, such as torque arms 272 and 274, the difference in the asymmetrical torque limit may be a factor of two (i.e., twice as much torque can be applied in the second direction of rotation 266 than in the first direction of rotation 264). Reversing the relative orientation of the torque arms 272 and 274 would achieve an opposite asymmetrical torque limit (i.e., a higher torque limit in the first direction of rotation 264 rather than the second direction of rotation 266).

In accordance with certain embodiments presented herein, the entire torque limiting drive tool 250, including the handle 252 and the torque arms 272 and 274, are a unitary (one-piece) structure. Such a unitary structure may be formed via a molding (e.g., injection molding) process, via a milling process, etc. In certain embodiments, the entire torque limiting drive tool 250, including the handle 252 and the torque arms 272 and 274 is formed from an at least semi-rigid polymeric (e.g., plastic) material. In the example of FIGS. 2A-2E, the outer surface 285 includes a flat portion 281, which may enable the tool to be placed on a surface without rolling away.

Figure 3:
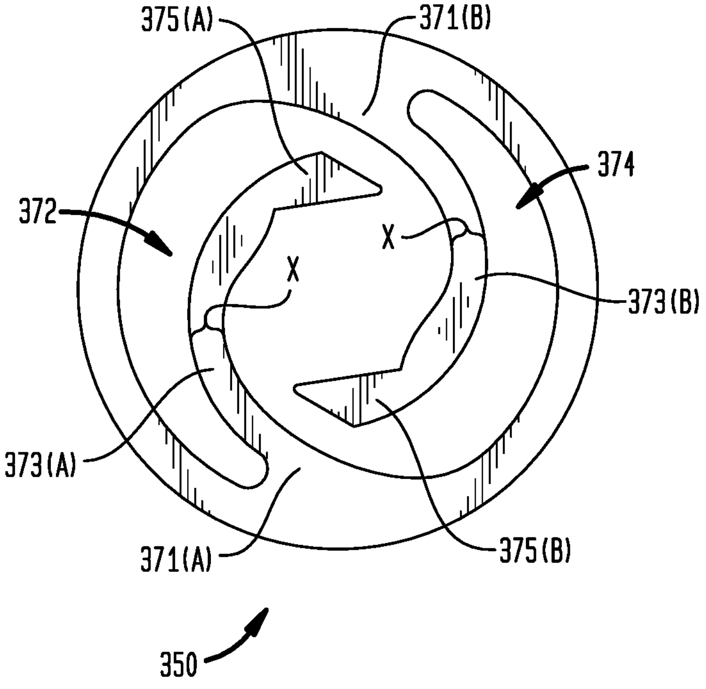
FIG. 3 is top-view of a distal end of a torque limiting drive tool, in accordance with certain embodiments presented herein.
Figure 4:
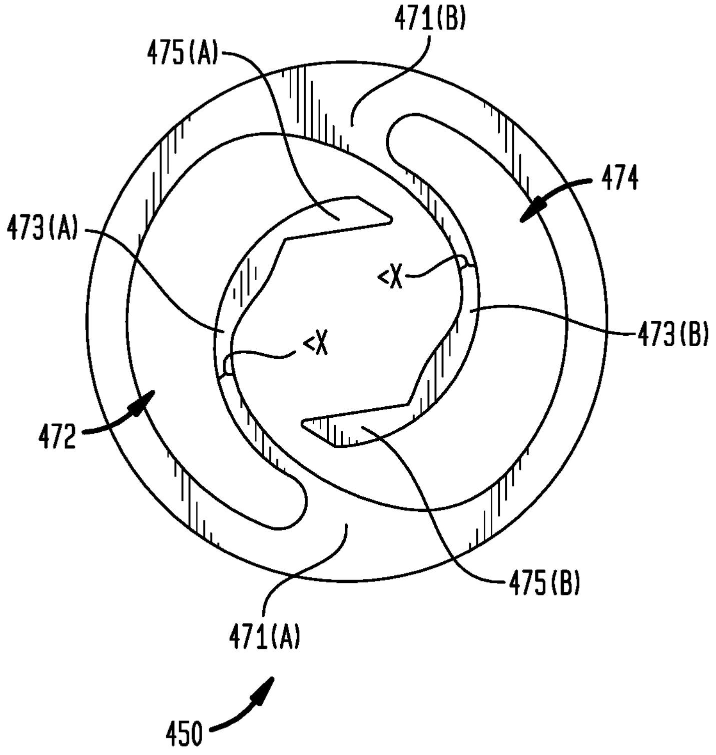
FIG. 4 is top-view of a distal end of a torque limiting drive tool, in accordance with certain embodiments presented herein.
Figure 5:
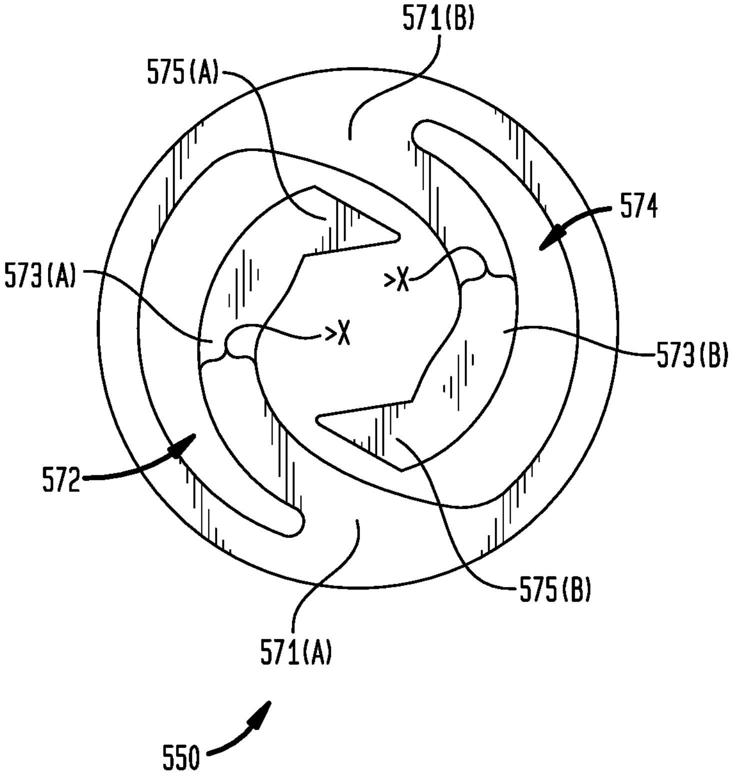
FIG. 5 is top-view of a distal end of a torque limiting drive tool, in accordance with certain embodiments presented herein.

As noted, the maximum torque limit of the torque limiting drive tool 250 (i.e., the amount of torque that can be applied by the torque arms 272 and 274) in each of the first direction of rotation 264 and the second direction of rotation 266 is determined by the material properties, structural arrangement, and relative orientation of the torque arms 272 and 274. One aspect of the structural arrangement of the torque arms 272 and 274 that determines the maximum torque limit is the cross-sectional thickness of the torque arms 272 and 274. As such, the maximum torque limit of a torque limiting drive tool having an arrangement as shown in FIGS. 2A-2D can be adjusted by forming the torque arms with different thicknesses. FIGS. 3, 4, and 5 are schematic diagrams illustrating different arrangements each having different thickness torque arms.

As noted above, torque arms in accordance with certain embodiments presented herein can have a varying thickness along the transverse/lateral direction of the arms. As such, merely for ease of description, FIGS. 3, 4, and 5 are described with reference to the thickness of a central region of each torque arm. It would be appreciated that the thickness of the first and second ends in each of FIGS. 3, 4, and 5 could correspondingly vary along the transverse length thereof in manners similar to that as described above with reference to FIGS. 2A-2E.

Referring first to FIG. 3, shown is the distal end of a torque limiting drive tool 350 comprising a torque arm 372 having a first end 371(A) and a second end 375(A) that are connected by a central region 373(A). The central region 373(A) has a cross-sectional thickness "X." The torque limiting drive tool 350 also comprises a torque arm 374 having a first end 371(B) and a second end 375(B) that are connected by a central region 373(B). The central region 373(B) also has a cross-sectional thickness "X."

Referring next to FIG. 4, shown is the distal end of a torque limiting drive tool 450 comprising a torque arm 472 having a first end 471(A) and a second end 475(A) that are connected by a central region 473(A). The central region 473(A) has a cross-sectional thickness that is less than "X" (<X). The torque limiting drive tool 450 also comprises a torque arm 474 having a first end 471(B) and a second end 475(B) that are connected by a central region 473(B). The central region 473(B) also has a cross-sectional thickness that is less than "X" (<X).

Referring next to FIG. 5, shown is the distal end of a torque limiting drive tool 550 comprising a torque arm 572 having a first end 571(A) and a second end 575(A) that are connected by a central region 573(A). The central region 573(A) has a cross-sectional thickness that is greater than "X" (>X). The torque limiting drive tool 550 also comprises a torque arm 575 having a first end 571(B) and a second end 575(B) that are connected by a central region 573(B). The central region 573(B) also has a cross-sectional thickness that is greater than "X" (>X).

When comparing FIGS. 3, 4, and 5, the torque limiting drive tool 550 of FIG. 5 has the thickest torque arms 572 and 574 and, accordingly, has the highest maximum torque limit. However, torque limiting drive tool 450 of FIG. 4 has the thinnest torque arms 472 and 474 and, accordingly, has the lowest maximum torque limit. Torque limiting drive tool 350 of FIG. 3 has torque arms 372 and 374 with a thickness that is between that the torque limiting drive tools 450 and 550, this is also has a maximum torque limit that is between that of the tools of FIGS. 4 and 5.

FIGS. 3, 4, and 5 illustrate only one example technique for setting the maximum torque limits of a torque limiting drive tool, in accordance with embodiments presented herein. It is to be appreciated that other aspects of the torque arms (e.g., the material used to form the torque arms, the bias of the torque arms, the length of the torque arms, etc.) may be varied to provide for different maximum torque limits.

Figure 7:
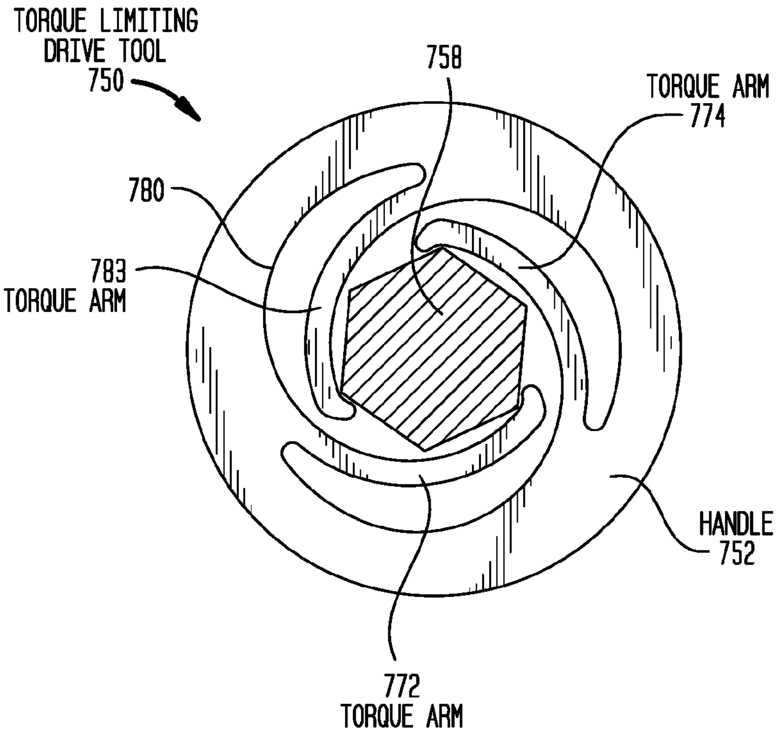
FIG. 7 is top-view of a distal end of a torque limiting drive tool, in accordance with certain embodiments presented herein.

FIGS. 2A-2D, as well as FIGS. 3, 4, and 5, have been described with reference to embodiments that comprise two torque arms. However, it is to be appreciated that the use of two torque arms is merely illustrative and that embodiments presented herein may include more than two torque arms. For example, FIG. 7 illustrates the distal end of a torque limiting drive tool 750 that is similar to the arrangements described above with reference to FIGS. 2A-2D, 3, 4, and 5. However, in this embodiment, the torque limiting drive tool 750 comprises three (3) torque arms, referred to as torque arms 772, 774, and 783. The torque arms 772, 774, and 783 may be similar to those described with reference to the embodiments of FIGS. 2A-2D, 3, 4, and 5, where the torque arms are attached to, and extend from, an inner surface 780 of a handle 752. For purposes of illustration, FIG. 7 illustrates a drive bit 858 positioned between the torque arms 772, 774, and 783.

As noted above, FIGS. 2A-2D, as well as FIGS. 3, 4, and 5, have been described with reference to torque limiting drive tools having torque arms located within the handle of the tool (e.g., torque arms directly mechanically attached an inner surface of a handle). In alternative embodiments, the torque arms may be connected to, and extend longitudinally from, the distal end of the handle.

Figure 6A:
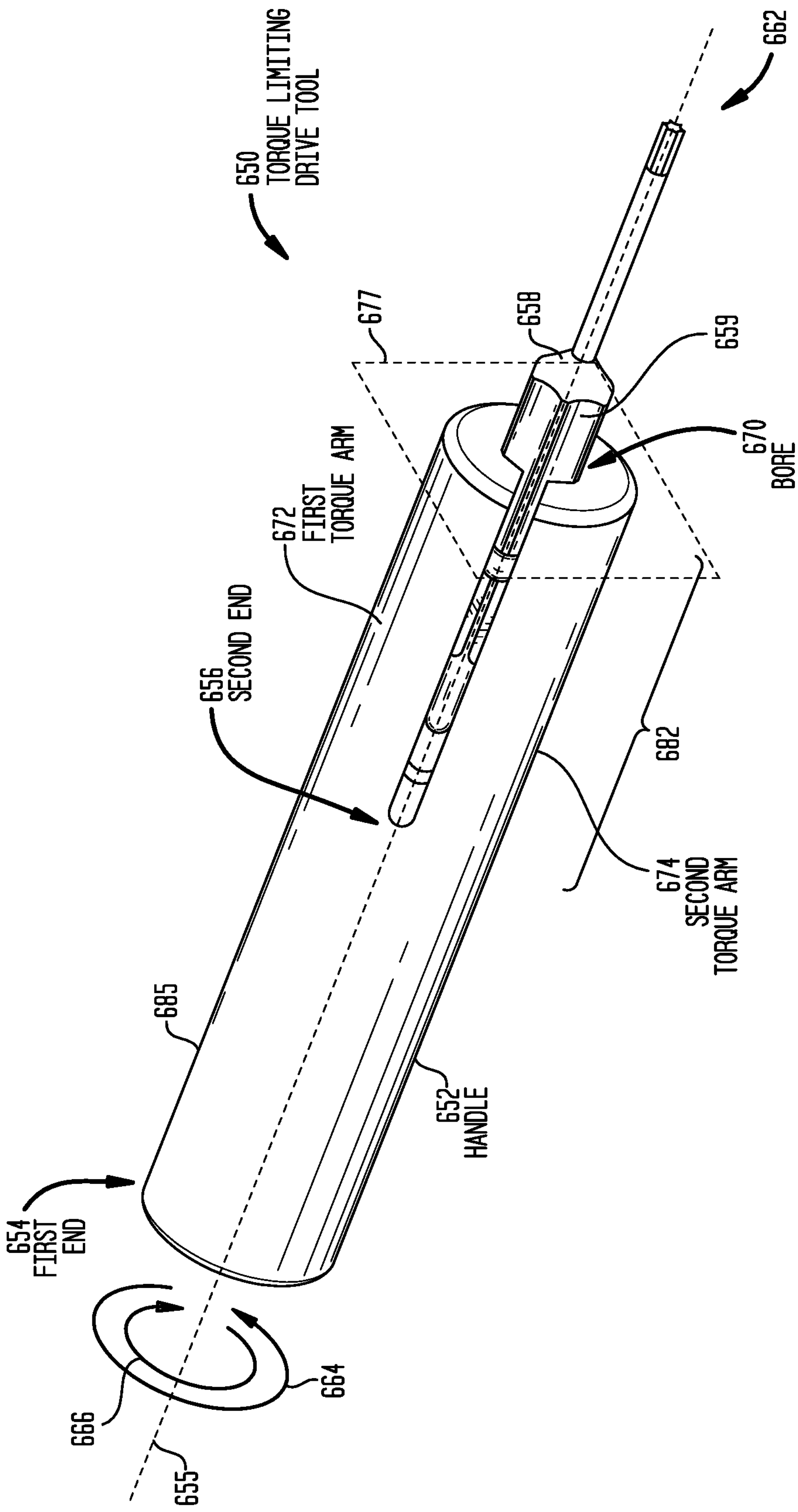
FIGS. 6A and 6B are perspective views of a torque limiting drive tool, in accordance with certain embodiments presented herein.
Figure 6B:
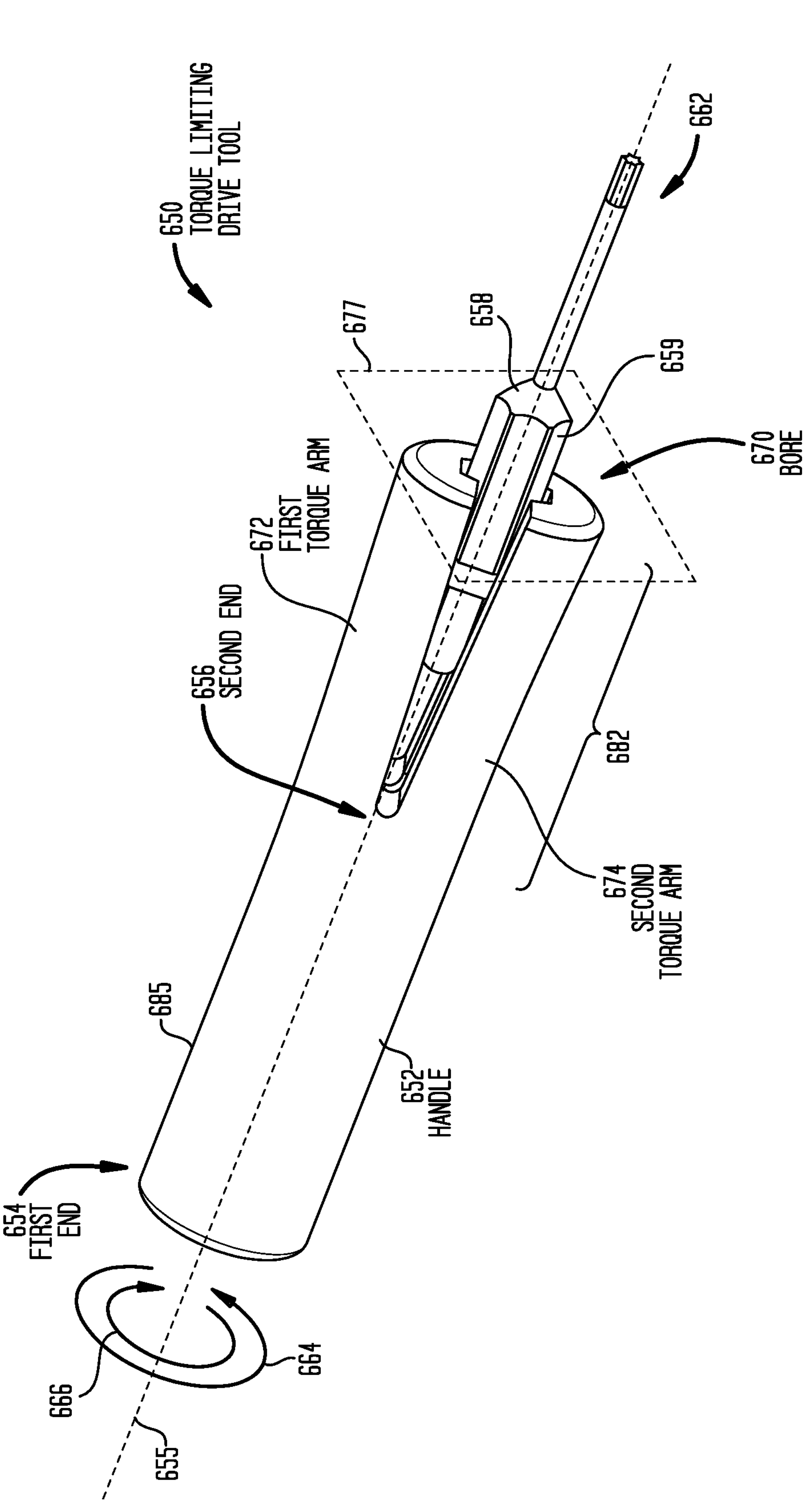

For example, FIGS. 6A and 6B illustrate one such torque limiting drive tool 650, in accordance with certain embodiments presented herein. For ease of description, torque limiting drive tool 650 is shown within a drive bit 658 inserted therein. FIG. 6A illustrates the torque limiting drive tool 650 in an arrangement in which the tool can exert a torque on the drive bit 658, while FIG. 6B illustrates an arrangement in which the tool has reached a maximum torque limit.

As shown, the torque limiting drive tool 650 comprises a handle 652 having a first (proximal) end 654 and a second (distal) end 656. Connected to the second end 656 are a first torque arm 672 and a second torque arm 674. In the embodiment of FIGS. 6A and 6B, the first torque arm 672 and the second torque arm 674 are connected to, and extend longitudinally from, the second end 656 of the handle 652. The torque arms 672 and 674 are also separated by a pair of elongate, axially extending slots 661 (e.g., extend generally parallel to the elongate axis 655). That is, the torque arms 672 and 674 are separated from one another on both sides of a central axis 655 of the tool. The two slots 661 are generally symmetrical, but positioned on opposing sides of the central axis 655

The first torque arm 672 and the second torque arm 674 collectively define/form a bore 670 that is configured (e.g., shaped and dimensions) so as to longitudinally (axially) receive the drive bit 658 therein. That is, the tool 650 has an elongate central axis 655 and the bore 670 is positioned such that the drive bit 658 may be received along, or generally parallel to, the elongate axis 655 (e.g., the bore 670 is centered on the elongate central axis 655 or offset from the elongate central axis 655). When inserted, the elongate length of the drive 658 is also generally parallel to the elongate slots 661.

As noted, the bore 670 is defined/formed by the first torque arm 672 and the second torque arm 674. Each of the torque arms 672 and 674 generally general arched or curved cross-sectional shape (e.g., along/within/parallel to a plane 677 that is generally transverse to elongate axis 655) and face one another. Also as noted, the bore 670 is configured to axially/longitudinally receive the drive bit 658 therein. The bore 670 has a size (e.g., dimensions) and shape, formed by the torque arms 672 and 674, that generally corresponds to the size and shape of outer surface 659 of the drive bit 658 (e.g., the bore 670 is configured to mate with the drive bit 658. In addition, the torque arms 672 and 674 are each biased towards the center (e.g., axis 655) of the bore 670.

As shown, the torque arms 672 and 674 each have a length 682 extending from the handle 652 (e.g., a length that is generally parallel to the elongate axis 655). One or both of the torque arms 672 and 674 also includes an end-stop (not shown in FIGS. 6A and 6B) that terminates the insertion of the drive bit 658. That is, the drive bit 658 is inserted into bore 670, the end of the drive bit 658 will be positioned abutting the end-stop(s). In this position, the entire length 682 of each of the torque arms 672 and 674 will be abutting the outer surface 659 of the drive bit 658. As such, when the drive bit 658 is fully inserted into the bore 670 (inserted such that the end of the drive bit 658 abuts the end-stop(s)), the torque arms 672 and 674 (along the entire length 682 thereof) will apply a slight compressive force on the outer surface 659 of the drive bit 658 to grip the drive bit.

Once the drive bit 658 is fully inserted into the bore 670, a distal drive head 662 of the drive bit is mated with a screw head of a component of a medical device. In operation, a user applies a manual rotation force to an outer surface 685 of the handle 652 to cause the handle to rotate in either a first direction of rotation, represented by arrow 664 in FIG. 6A, or a second direction of rotation, represented by arrow 666 in FIG. 6A. Since the torque arms 672 and 674 are directly mechanically attached to the handle 252, and because the torque arms 672 and 674 are abutting the drive bit 658, rotation of the handle 652 in either the first direction of rotation 664 or the second direction of rotation 666 will cause corresponding rotation of the drive bit 658 in the same rotational direction. That is, the torque arms 672 and 674 are configured (e.g., biased towards the opening) so as to exert a torque on the drive bit 658 in direct response to rotation of the handle 652 in each of the first direction of rotation 664 or the second direction of rotation 666. However, the torque arms 672 and 674 are configured such that only a limited amount of torque may be applied the drive bit 658 in each of the first direction of rotation 664 or the second direction of rotation 666.

More specifically, the torque arms 672 and 664 are configured such that if the torque (rotational force) exerted by the handle 652 onto the drive bit 658 (via the torque arms 672 and 674) exceeds a predetermined threshold, sometimes referred to as a "maximum rotational force" or a "maximum torque limit," then the torque arms 672 and 674 will deflect/flex away from the bore 670 (and the outer surface 659 of the drive bit 658) causes the torque arms 672 and 674 (and attached handle 652) to slip or rotate around the outer surface 659 of the drive bit 658. Therefore, since the torque arms 672 and 674 rotate around the outer surface 659, the torque arms are unable to apply any additional torque on the drive bit 658. FIG. 6B illustrates that, when the maximum torque limit, is reached the slots 661 bend open and the drive bit 658 rotates independently from the torque arms (e.g., rotates ⅙ turn).

The rotation of the torque arms 672 and 674, and the attached handle, around the outer surface 659 of the drive bit 658 provides the user with a haptic indication that the maximum torque limit has been reached (e.g., the user can manually feel the relatively free spinning of the handle 652). However, the rotation of the torque arms 672 and 674 around the outer surface 659 of the drive bit 658 may also emit an audible "click" sound, which provides the user within an audible indication that the maximum torque limit has been reached. That is, the tool 650 is configured such that reaching the maximum torque limit causes a sudden drop in the torque when the torque arms "steps over" (e.g., rotate around) the drive bit 658. This provides not only a clear audible sound, but also detectable haptic feedback.

In the embodiments of FIGS. 6A and 6B, the material properties and structural arrangement of the torque arms 672 and 674, as well as the configuration of the slots 661, determines/sets the maximum torque limit in each of the direction of rotation 664 or the second direction of rotation 666. In certain embodiments, the torque arms 672 and 674 are configured such that the amount of torque exerted on the drive bit 658 in each of the first direction of rotation 664 and the second direction of rotation 666 is substantially the same.

One aspect of the structural arrangement that determines the maximum torque limit is the elongate length of the slots 661. In particular, a longer relative length for the slots 661 results in a lower maximum torque limit. Another aspect of the structural arrangement that determines the maximum torque limit is material properties of the arms (e.g., the strength of the material forming the arms). Yet another aspect of the structural arrangement that determines the maximum torque limit is the cross-sectional thickness of the torque arms 672 and 674.

In accordance with certain embodiments presented herein, the entire torque limiting drive tool 650, including the handle 652 and the torque arms 672 and 674, are a unitary (one-piece) structure. Such a unitary structure may be formed via a molding (e.g., injection molding) process, via a milling process, etc. In certain embodiments, the entire torque limiting drive tool 650, including the handle 652 and the torque arms 672 and 674 is formed from an at least semi-rigid polymeric (e.g., plastic) material.

Figure 8:
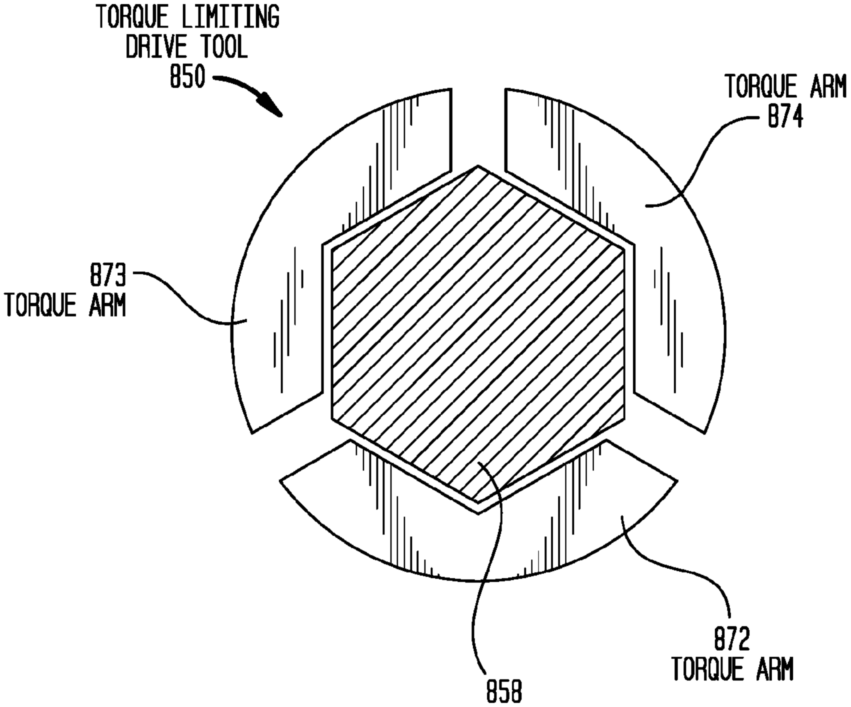
FIG. 8 is top-view of a distal end of a torque limiting drive tool, in accordance with certain embodiments presented herein.

FIGS. 6A and 6B have been described with reference to embodiments that comprise two torque arms. However, it is to be appreciated that the use of two torque arms is merely illustrative and that embodiments presented herein may include more than two torque arms. For example, FIG. 8 illustrates a torque limiting drive tool 850 that is similar to the arrangements described above with reference to FIGS. 6A and 6B. However, in this embodiment, the torque limiting drive tool 850 comprises three (3) torque arms, referred to as torque arms 872, 874, and 883. The torque arms 872, 874, and 883 may be similar to those described with reference to the embodiments of FIGS. 6A and 6B, where the torque arms extend from the second end (not shown in FIG. 8) of a handle (also not shown in FIG. 8). For purposes of illustration, FIG. 8 illustrates a drive bit 858 positioned between the torque arms 872, 874, and 883.

As explained elsewhere herein, torque limiting drive tools in accordance with certain embodiments presented herein could be used in a number of different manners for a number of different purposes. For example, the torque limiting drive tools presented herein may be used with other auditory prostheses, including other bone conduction devices, cochlear implants, middle ear auditory prostheses, direct acoustic stimulators, auditory brain stimulators, etc. The torque limiting drive tools presented herein may also be used with bone screws, vestibular devices (e.g., vestibular implants), visual devices (i.e., bionic eyes), sensors, pacemakers, drug delivery systems, defibrillators, functional electrical stimulation devices, catheters, seizure devices (e.g., devices for monitoring and/or treating epileptic events), sleep apnea devices, electroporation devices, etc.

It is to be appreciated that the embodiments presented herein are not mutually exclusive and that the various embodiments may be combined with another in any of a number of different manners.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A torque limiting drive tool, comprising:

an elongate handle having a proximal end and a distal end; and at least first and second torque arms located at the distal end of the elongate handle and defining a bore configured to longitudinally receive a drive bit therein, wherein the at least first and second torque arms are each directly mechanically attached to the elongate handle and configured to exert a torque on the drive bit in direct response to rotation of the elongate handle in each of a first direction of rotation and a second direction of rotation, and wherein the torque exerted by the at least first and second torque arms has an associated first maximum torque limit in the first direction of rotation and an associated second maximum torque limit in the second direction of rotation, wherein the second maximum torque limit is greater than the first maximum torque limit.

2. The torque limiting drive tool of claim 1, wherein the at least first and second torque arms are biased inwards toward the bore to apply a compressive force on the drive bit inserted into the bore.

3. The torque limiting drive tool of claim 1, wherein the second maximum torque limit is approximately two times greater than the first maximum torque limit.

4. The torque limiting drive tool of claim 1, wherein upon reaching each of the first and second maximum torque limits, the at least first and second torque arms are configured to rotate around an outer surface of the drive bit.

5. The torque limiting drive tool of claim 4, wherein the torque limiting drive tool is configured to emit an audible click when the at least first and second torque arms rotate around the outer surface of the drive bit.

6. The torque limiting drive tool of claim 1, wherein the at least first and second torque arms each have a first end connected to an inner surface of the elongate handle and each extend a transverse distance from the inner surface of the elongate handle to a second end.

7. The torque limiting drive tool of claim 6, wherein the at least first and second torque arms each have a thickness that changes between the first end and the second end.

8. The torque limiting drive tool of claim 6, wherein the at least first and second torque arms each have a curved cross-sectional shape within a plane that is generally transverse to an elongate axis of the elongate handle.

9. The torque limiting drive tool of claim 6, wherein the at least first and second torque arms have symmetrical shapes, but are oriented in opposing directions such that the second ends of each of the at least first and second torque arms face one another across the bore.

10. The torque limiting drive tool of claim 1, wherein the at least first and second torque arms have a predisposition to flex inward towards a center of the bore in response to rotation of the elongate handle in the second direction of rotation and a predisposition to flex outward from the center of the bore in response to rotation of the elongate handle in the first direction of rotation.

11. The torque limiting drive tool of claim 1, wherein the at least first and second torque arms each extend longitudinally from the distal end of the elongate handle substantially parallel to an elongate axis of the elongate handle, and wherein the at least first and second torque arms are separated by a pair of elongate slots.

12. The torque limiting drive tool of claim 11, wherein the at least first and second torque arms each have a generally curved cross-sectional shape.

13. The torque limiting drive tool of claim 1, wherein the at least first and second torque arms comprise at least three torque arms.

14. A torque limiting drive tool, comprising:

a body having an elongate axis of rotation;

an opening at a first end of the body configured to receive a drive bit along the elongate axis of rotation; and a plurality of torque arms substantially surrounding the opening, wherein the plurality of torque arms is configured to grip the drive bit within the opening and to exert up to a first maximum rotational force on the drive bit in a first rotational direction and up to a second maximum rotational force on the drive bit in a second rotational direction, and wherein the plurality of torque arms has a predisposition to flex inward towards a center of the opening in response to rotation of the body in the second rotational direction and a predisposition to flex outward from the center of the opening in response to rotation of the body in the first rotational direction.

15. The torque limiting drive tool of claim 14, wherein upon reaching each of the first maximum rotational force and the second maximum rotational force, the plurality of torque arms is configured to rotate around an outer surface of the drive bit.

16. The torque limiting drive tool of claim 15, wherein the torque limiting drive tool is configured to emit an audible click when the plurality of torque arms rotates around the outer surface of the drive bit.

17. The torque limiting drive tool of claim 14, wherein each torque arm of the plurality of torque arms has a first end connected to an inner surface of the body and extends a transverse distance from the inner surface of the body to a second end.

18. The torque limiting drive tool of claim 17, wherein each torque arm of the plurality of torque arms has a curved cross-sectional shape within a plane that is generally transverse to the elongate axis of rotation.

19. The torque limiting drive tool of claim 17, wherein torque arms of the plurality of torque arms have symmetrical shapes, but are oriented in opposing directions such that the second ends of each of the plurality of torque arms face one another across the opening.

20. The torque limiting drive tool of claim 14, wherein each torque arm of the plurality of torque arms extends longitudinally from a distal end of the body substantially parallel to the elongate axis of rotation, and wherein torque arms of the plurality of torque arms are separated by a pair of elongate slots.

21. The torque limiting drive tool of claim 14, wherein the plurality of torque arms comprises only two torque arms.

22. A medical tool, comprising:

a handle having an axis of rotation; and two or more torque arms located at a distal end of the handle and forming a bore to receive a drive bit along the axis of rotation, wherein the two or more torque arms are each connected to the handle and biased towards the bore to exert a torque on the drive bit in direct response to rotation of the handle about the axis of rotation, wherein the two or more torque arms extend radially inward from an inner surface of the handle to define respective spaces between the two or more torque arms and the inner surface, and wherein the two or more torque arms are configured to flex outward toward the inner surface to close the respective spaces while exerting torque on the drive bit to establish an associated first torque limit in a first direction of rotation about the axis of rotation and an associated second torque limit in a second direction of rotation about the axis of rotation such that the torque exerted by the two or more torque arms has an asymmetrical torque limit about the axis of rotation.

23. The medical tool of claim 22, wherein the asymmetrical torque limit is approximately two times greater in a second rotational directional axis of rotation than in a first rotational direction about the axis of rotation.

24. The medical tool of claim 22, wherein upon reaching each asymmetrical torque limit in each of a first rotational direction about the axis of rotation and a second rotational direction about the axis of rotation, the two or more torque arms are configured to rotate around an outer surface of the drive bit.

25. The medical tool of claim 22, wherein the two or more torque arms each have a first end connected to the inner surface of the handle and each extend a transverse distance from the inner surface of the handle to a second end.

26. The medical tool of claim 25, wherein the two or more torque arms each have a curved cross-sectional shape within a plane that is generally transverse to an elongate axis of the handle.

27. The medical tool of claim 22, wherein the two or more torque arms have symmetrical shapes each comprising a first end connected to the handle and a second end, wherein the two or more torque arms are oriented in opposing directions such the second ends of each of the two or more torque arms face one another across the bore.

28. The medical tool of claim 22, wherein the two or more torque arms have a predisposition to flex inward towards a center of the bore in response to rotation of the handle in the second direction of rotation about the axis of rotation and a predisposition to flex outward from the center of the bore in response to rotation of the handle in the first direction of rotation about the axis of rotation.

29. The medical tool of claim 22, wherein the two or more torque arms are attached to the handle.

30. The medical tool of claim 22, wherein the two or more torque arms comprise:

a first torque arm having a first end extending from the inner surface of the handle; and a second torque arm having a second end extending from the inner surface of the handle, wherein the first torque arm extends toward the second end of the second torque arm, and the second torque arm extends toward the first end of the first torque arm.

* * * * *